United States Patent
Kuennecke

(10) Patent No.: US 6,183,418 B1
(45) Date of Patent: Feb. 6, 2001

(54) PROCESS AND MEASURING SYSTEM FOR DETECTION OF SUBSTANCES EMITTED OR PERSPIRED THROUGH THE SKIN

(75) Inventor: Wolfgang Kuennecke, Braunschweig (DE)

(73) Assignees: Trace Analysensysteme GmbH, Braunschweig; Moller Feinmechanik GmbH & Co., Fulda; META Mebtechnische Systeme GmbH, Altenberge, all of (DE)

(*) Notice: Under 35 U.S.C. 154(b), the term of this patent shall be extended for 0 days.

(21) Appl. No.: 09/015,911

(22) Filed: Jan. 30, 1998

(51) Int. Cl.$^7$ ......................................... A61B 5/00
(52) U.S. Cl. ............................................... 600/363
(58) Field of Search ................... 600/363–364, 600/358

(56) References Cited

U.S. PATENT DOCUMENTS 4,809,698 * 3/1989 Kogo ..................................... 600/364

FOREIGN PATENT DOCUMENTS

| | | |
|---|---|---|
| 25 39 771 | 3/1977 | (DE) . |
| 2539771 | 3/1977 | (DE) . |
| 31 37 765 A1 | 3/1983 | (DE) . |
| 3137765 A1 | 3/1983 | (DE) . |
| 33 09 458 A1 | 9/1983 | (DE) . |
| 3309458 A1 | 9/1983 | (DE) . |
| 34 22 233 A1 | 12/1985 | (DE) . |
| 40 34 446 A1 | 5/1991 | (DE) . |
| 4034446 A1 | 5/1991 | (DE) . |
| 40 07 246 A1 | 9/1991 | (DE) . |
| 4007246 A1 | 9/1991 | (DE) . |
| 41 25 739 A1 | 2/1993 | (DE) . |
| 4125739 A1 | 2/1993 | (DE) . |
| 3422233 A1 | 12/1995 | (DE) . |
| 196 17 964 C2 | 11/1997 | (DE) . |
| WO 94/07407 | 4/1994 | (WO) . |
| WO94/07407 | 4/1994 | (WO) . |

OTHER PUBLICATIONS

Mohns et al., "Bestimmung der Ethanolkonzentration in Bier und Wein mittels Fliebdiffusions—Analyse und elektrochemischer Detektion"; Deutsche Lebensmittel-Rundschau, No. 1, Jan. 1996; pp. 1–4.

8$^{th}$ Int. Symposium on Non–Linear Electromagnetic Systems, Braunschweig May 12–14, 1987, Symposium Proceedings, 1998.

Buttgenbach, S. et al., "Pen–sized Alcohol Meter: Alcopen," Medical Applications, p. 17, 1997.

Translation for The Institute for Microtechnology of the Braunschweig Technical University.

Dr. K.G. Bernger; Deutsche Lebensmittel–Rundschau; No. 1, Jan. 1996 92 ed. pp. 1–4.

* cited by examiner

Primary Examiner—Cary O'Connor
Assistant Examiner—Michael Astorino
(74) Attorney, Agent, or Firm—McGuire, Woods, Battle & Boothe, LLP

(57) ABSTRACT

The process for detection and for quantitative determination of substances emitted or perspired through the skin is derived from flow diffusion analysis. The measuring system conceived for this purpose uses a diffusion half cell through which an acceptor medium flows and which is closed by a membrane. For the duration of the measurement, the membrane is brought into contact with the skin or a closed gas volume formed over the skin. With the process and the related measuring system, the blood alcohol level can be determined with a good degree of precision indirectly via the quantity of (gaseous) ethanol emitted through the skin.

13 Claims, 3 Drawing Sheets

5a)

5b)

5c)

PROCESS AND MEASURING SYSTEM FOR DETECTION OF SUBSTANCES EMITTED OR PERSPIRED THROUGH THE SKIN

BACKGROUND OF THE INVENTION

1. Field of the Invention

The present invention relates to a process and a measuring system for detection of substances emitted or perspired through the skin, in particular alcohol, by means of a detection system responding to the substances.

2. Background Description

Precisely in the fields of foodstuff analysis and medicine, there is a constant need for new, easy to handle, reliable analyzing methods for detection of the widest variety of substances. In some fields of application there is also the need for the related analyzing equipment to be easy to transport, to make on-site analysis possible. In addition, the criterion of cost often plays a role, and for this reason, processes and measuring equipment that are particularly inexpensive to operate are also in demand.

For traffic control by the police, a simple, reliable and adequately precise test for a quick assessment of blood alcohol level during road checks is still being sought. The test for blood alcohol level via the breath conducted thus far firstly presupposes the active cooperation of the driver and in addition, it can be considerably distorted by numerous outside influences.

The technical problem on which the invention is based consists in first finding in general, a reliable, easy to handle, sufficiently precise analyzing process for quantitative determination of small quantities of substances in a solution or in a gas phase with suitable detectors, that is appropriate to indirectly determine the blood alcohol level.

A further technical problem of the invention consists in developing for this process a measuring system that is as transportable as possible, and easy and safe to operate.

SUMMARY OF THE INVENTION

According to an aspect of the invention, this technical problem is solved by a transportable measuring system for detection of substances emitted or perspired through the skin, by flow diffusion analysis, by means of a detection system responding to these substances, whereby the flow diffusion analysis unit arranged in the measuring system consists of:

means for stocking up and conveying an acceptor solution (50, 10, 20, 30, 70), means for controlling the volume flow of the acceptor solution (40, 60, 200), a diffusion analysis half cell (80), consisting of a chamber for receiving the acceptor solution and a membrane (81) closing this chamber and permeable to the substance to be detected, a chamber designed in front of the membrane and open toward the outside for forming a closed gas volume between the skin and the membrane under measuring conditions, a detection system (90) for detection of the substance to be detected, and means for evaluating and displaying the measuring results.

According to another aspect of the invention, the technical problem is solved by a transportable measuring system for detection of substances emitted or perspired through the skin, by flow diffusion analysis, by means of a detection system responding to these substances, whereby the flow diffusion analysis unit arranged in the measuring system consists of:

means for stocking up and conveying an acceptor solution (50, 10, 20, 30, 70), means for controlling the volume flow of the acceptor solution (40, 60, 200), a diffusion analysis half cell (80), consisting of a chamber for receiving the acceptor solution and a membrane (81) closing this chamber and permeable to the substance to be detected, a detection system (90) for detection of the substance to be detected, means for evaluating and displaying the measuring results, and a replaceable part (measuring head) that comprises the membrane (81), with parts of the flow diffusion analysis unit.

Furthermore, the technical problem is solved by a process for detection of substances emitted or perspired through the skin, in particular alcohol, by means of a detection system by flow diffusion analysis, responding to these substances, whereby for the duration of the sampling, a membrane arranged in a replaceable measuring head is placed directly onto the skin of a person to be examined or is brought into contact with a closed gas volume formed over the skin, whereby a diffusion half cell is used which is closed with the membrane and through which an acceptor medium flows, and whereby the acceptor solution loaded with the substance to be detected is fed to the detection system.

With the modified flow diffusion analysis presented in this case, it is a matter of a process derived from the known flow diffusion analysis.

In this connection, the known process of flow diffusion analysis is modified in such a way that the membrane of a diffusion half cell through which acceptor medium flows is brought directly into contact with a skin surface evaporating/perspiring the substance or a gas volume formed over the skin.

A quantity of alcohol correlating to the blood alcohol level is emitted through the skin and is measured there by placing the membrane of the half cell onto the skin.

The principle of flow diffusion analysis is known for the example of an ethanol concentration determination in beer and wine, it is described in: J. Mohns, W. Kuennecke, "Deutsche Lebensmittel-Rundschau", *German foodstuff review*, 92nd year (1996), pp. 1–4.

The setup described therein for the flow diffusion analysis consisted of a 2-channel pump, two 3/2-port directional valves, a tempered diffusion cell with hydrophobic gas diffusion membrane, an enzyme reactor, a thick-layer electrode in a "wall jet" flow cell, and a potentiostat for electrochemical detection. The control and data recording takes place via computer. The principle of conventional FDA consists in that a continuous donor stream (sample/standard) is conveyed at a specific rate of flow through the diffusion cell (tempered if necessary), while an acceptor flow (in the example 0.1 in potassium phosphate buffer pH 7.5) is pumped at the same rate of flow on the other side of the membrane through the diffusion cell. For the analysis, in general the acceptor flow is stopped in the diffusion cell for a certain period of time by switching the valves, in such a way that the substance to be measured, ethanol in this case, can diffuse through the membrane from the donor flow into the acceptor medium. The quantity of ethanol diffused through the membrane is dependent on the layer thickness/pore size of the membrane, the stopping time (accumulation time) and the concentration gradient over the membrane. After switching the valves again, the volume element enriched with ethanol in the acceptor is further conveyed to the detection.

The described principle of flow diffusion analysis has the disadvantage that the donor flow must be separately controlled, necessitating a more expensive setup in terms of equipment. For this reason, flow diffusion analysis is less suitable for quick tests on different samples.

From DE 41 25 739 A1, a device and a process are known for sampling and measuring samples from a number of different measuring points; this is intended and suitable for the monitoring of air in a space. Samples are taken at different collecting points in the space, at which the air samples are introduced via valves or membranes into a collecting pipe and inside it, they are fed with a carrying medium to a sensor. In the case of this system. it is a matter of a large, stationary system, such that the principles of the related process cannot easily be transferred to a transcutaneous blood alcohol measurement on the skin of a test subject.

From DE 33 09 458 A1, a measuring process is also known for the concentration of combustible components in a liquid or a gas; in it, a sampler of a membrane permeable to gas, for example a plastic hose, is inserted into the gas chamber of a reactor boiler and combustible components diffusing in are fed to a semiconductor gas sensor with pure oxygen as carrier gas. In this case as well, only a purely stationary system is described.

From DE 31 37 765 A1, a process and a system are known for quick detection, identification and quantification of trace elements in gases, liquids and solids; in it, a collecting surface for receiving and collecting trace elements is mounted on the contact membrane, beatable and swept with carrier gas from behind, of an input head of a gas-phase chromatograph. The disadvantage of this likewise stationary system consists primarily in that in separate steps, the trace elements to be examined are first absorbed on the collecting surface and subsequently desorbed again by annealing and must be fed to the flow of carrier gas.

This process is relatively costly and also requires a costly evaluation in order for an original concentration to be inferred from the accumulating adsorption.

On the other hand, from WO 94/07407 A1, a blood alcohol monitoring system is known; it is intended to make possible the continuous monitoring of people's blood alcohol level with the aid of a transcutaneous sensor unit. In this connection, a sampling cell containing the sensor is placed onto the skin; toward the skin side, it is closed with a membrane permeable to alcohol. This system does not work with a flowing conveyance medium on the acceptor side, in such a way that in principle, concentration or sensitivity differences in the sample cannot be entered into by adjusting an acceptor volume flow.

U.S. Pat. No. 4,809,698 shows a transcutaneous blood gas sensor that operates similarly. This system is essentially limited to a sensor holder that can be placed on the skin, whereby the electrochemically operating sensor is closed with a membrane retaining the electrolyte solution. In this case as well, no influence on the sampling is possible.

The process according to the invention and the measuring system now make it possible, within a flow diffusion process, to work with diffusion half cells—in a manner similar to that known from the above-mentioned sensor cells. In this connection, the diffusion half cell, through which an acceptor medium flows and which is closed with a membrane permeable to the substance to be detected, is brought into contact at least for the duration of the measurement with the substance evaporated or perspired in gaseous form. The flow of volume of the acceptor medium is controlled with suitable means in such a way that the quantity of substance diffused into the acceptor during the measuring period is sufficiently large for the exact detection.

In this connection, it is also possible to place the membrane of the diffusion half cell directly onto the skin, for example for detection of alcohol, whereby the alcohol perspired through the skin correlates closely to the blood alcohol level.

The acceptor flow can be kept in the diffusion half cell during the measurement for a certain period of time, in order to bring about in the acceptor medium a defined enrichment of the substance to be detected.

Under certain circumstances, it may be advantageous to create a small, closed-off gas space between the membrane of the half cell and the skin of the person to be examined; the alcohol diffuses through this space over a short distance up to the membrane, in order to minimize influences of skin irregularities.

A biosensor is preferably used as a detection system. Biosensors for detection of various substances are known in literature. Alcoholoxidase (AOD) is preferably used for the detection of alcohol, whereby the equimolecular-formed hydrogen peroxide is determined electrochemically or amperometrically at an electrode preferably a platinum thick-layer electrode. In this connection, the alcohol-oxidase may be immobilized with the glutaraldehyde method against "controlled pore gas" (CPG) and be present in a separate enzyme reactor, or the thick-layer electrode can be coated directly with the enzyme. In addition, in an alternative process execution, it can be provided for that the enzyme and/or a detection reagent, is added directly to the acceptor medium in such a way that subsequently (at the detector) only the detection reaction is detected, e.g. with electrochemical or optical means.

As an alternative, a biosensor operating with alcohol dehydrogenase (ADH) can also be considered.

In the case of quantitative measurements, it is provided for that the system is calibrated with external or internal means before the measuring.

The measuring system used for execution of the process is also considerably simplified compared to a classic FDA (flow diffusion analysis) setup.

For quantitative measurement, a calibrating unit can be provided for, unless work is being done with an external calibrating unit. The calibrating unit may comprise a standard solution, refillable or replaceable if necessary.

The measuring system preferably has a replaceable measuring head that comprises the system's parts that can only be used for one measuring procedure. The measuring head is preferably attached fixed to a measuring system of a handy size, but it could also be connected by hose with a stationary measuring apparatus.

In the case of the measuring system—for hygienic reasons already the membrane is arranged in the replaceable measuring head because it comes into contact with the skin of the person to be examined and for this reason, it is advantageously replaced after each measurement.

The replaceable measuring head may also comprise a supply container already filled with the acceptor solution (e.g., a buffer solution).

It may furthermore contain the entire diffusion analysis half cell, the detection system, insofar as it cannot be used several times, and/or a waste receptacle for spent acceptor solution. Furthermore, the replaceable measuring head may also contain means for controlling the flow of volume of the acceptor solution.

For conveying the acceptor solution and for generating a flow of volume (constant throughout the measuring) of the acceptor medium, all means suitable for this purpose may be used. In particular, a pump may be used that can be utilized for the precise controlling of the acceptor volume, including any stop times.

As an alternative, it is also possible to use simpler, mechanical pressure-generating means such as a mechanical hand pump connected with means for pressure regulation, i.e., valves, throttle sections and the like, for generating and maintaining uniform the acceptor volume flow during the measuring period.

For a transportable measuring system as handy as possible, it is strived to have the components of the measuring system sized small. At the same time, the sensitivity of the process increases when the substance to be detected is enriched in a smaller acceptor volume. For this reason, it is preferably provided for that the means for conveying the acceptor solution and for controlling the flow of volume are microfluid components.

Such microfluid components are known in microtechnology. For conveying and dosing small quantities of fluid in the range from a few nanoliters up to a few milliliters per minute, pumps, valves, flow systems and channels, flow sensors and pressure sensors can be produced with the aid of microtechnology production processes, for example in silicon micromechanics. Particularly advantageous in this regard are the high precision and the inexpensive production of the components for large numbers of units. The combination of sensor technology, actuator technology and signal processing can occur by connecting microfluid and microelectronic components.

The detection system may consist of an enzyme reactor and a subsequently added detector. Biosensors operating enzymatically are already known and in use today for detection of various substances. It can be expected that new biosensors will be constantly developed for other substances of interest. The detection of lactate or of various ions ill biological-medical systems could be of interest, for example.

For detection of alcohol/ethanol, there is the preferred biosensor in an enzyme reactor coated with alcohol oxidase (AOD) immobilized against "controlled pore glass" (CPG) if necessary. In this case, the ethanol is enzymatically converted with oxygen into acetaldehyde and hydrogen peroxide. The hydrogen peroxide formed equimolecular during the alcohol oxidase reaction is then quantitatively detected amperometrically on an electrode as detector, preferably a platinum thick-layer electrode at 700 mV.

As an alternative, the thick-layer electrode can be coated with the enzyme. The separate enzyme reactor is then dispensed with.

Particularly suitable as membranes are those of polydiethylsiloxane, native or modified polytetrafluoroethylene, polypropylene, typical organic materials—dialysis membranes for example—anorganic materials such as porous silicon, porous metal foils or silicate glasses, in particular in silicon-coated or hydrophobic form. Such membranes can be used for ethanol detection as well as for detection of other low-molecular substances. Generally speaking, hydrophobic membranes or support materials rendered hydrophobic or, respectively, membranes coated with hydrophobic material are suitable for ethanol detection. Other membranes that can be used advantageously are known to the experts from membrane technology. The layer thickness of the replacement layer, i.e., of the membrane itself or of the coating, may be from 1 to 2,000 $\mu$m, preferably from 10 to 1,000 $\mu$m.

BRIEF DESCRIPTION OF THE DRAWINGS

In the following, the invention is explained in greater detail with the help of the examples of construction illustrated in the drawings. These examples serve exclusively to explain the invention and are by no means meant or to understood as limitative. The drawings show.

DETAILED DESCRIPTION OF PREFERRED EMBODIMENTS OF THE INVENTION

FIGS. 1 through 4 show schematically different examples of construction of the measuring system according to the invention, whereby the same parts are designated by the same reference numbers in the individual figures.

Figure 1:
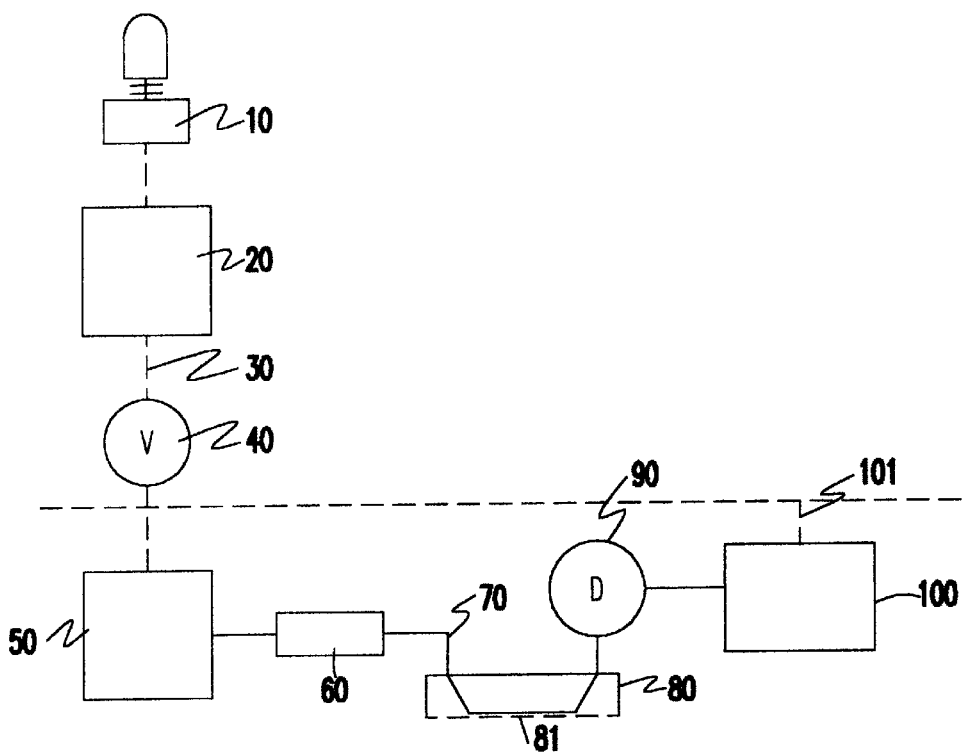
FIGS. 1–4 are a schematic illustration of four different examples of construction of the measuring system, whereby the removable measuring heads are equipped with different components in each case.

FIG. 1 shows a schematic illustration of a first example of construction. With simple mechanics 10, e.g., a small hand pump, pressure is delivered to a compressed-air reservoir 20. In this connection, the delivered pressure can reasonably be approximately up to 5 bar. The compressed-air line 30 leaving the compressed-air reservoir 20 runs via a valve 40, electronically controllable if necessary, in such a way that compressed-air dosed in a controllable manner can be fed to the acceptor supply reservoir 60. In this way, in collaboration with the throttle section 60—in this case a capillary section—the desired acceptor volume flow is generated in the line 70. The acceptor volume flow is guided by the diffusion half cell 80 that is closed with the membrane 81. During measuring, the enrichment acceptor solution with the substance diffused through the membrane 81 and to be detected takes place here in half cell 80.

Insofar as a detection reagent is added to the acceptor solution, the detection reaction—which is detected later in suitable manner, e.g., optically or in this case amperometrically, when passing through the detection system 90—also occurs already in the half cell.

The acceptor solution loaded with the substance to be detected is then fed to the detection system 90 which comprises, for example, the enzyme reactor and the related detection system—e.g., an electrode.

As an alternative, the enzyme can be directly connected with the detection system; for ethanol detection, the detection system 90 may be a platinum thick-layer electrode coated with alcohol oxidase.

The measuring data are also taken from the detection system 90 displayed (not shown here). From the detection system 90, the loaded acceptor solution is fed to a waste receptacle 100 which has the air evacuated from it at 101 for pressure compensation.

In addition to this basic schematic setup, for this example of construction it is provided for that the components arranged under the dotted line are comprised in a replaceable measuring head; in this way, they can be renewed after each measurement. In the present case, these are the acceptor supply reservoir 50 connected with the half cell 80 including membrane 81 via the throttle section 60, the detection system 90 and the waste receptacle 100.

This arrangement entails the advantage that the acceptor solution can be held in each case fresh in the replaceable measuring heads. The measuring system without the measuring head then remains "dry" and comprises only the mechanics (micromechancics should the occasion arise), the parts guiding the compressed-air and the display and evaluating electronics not shown in the drawings.

As FIGS. 2 and 3 described below show, however other divisions between the measuring system and the related measuring head are also possible.

Figure 2:
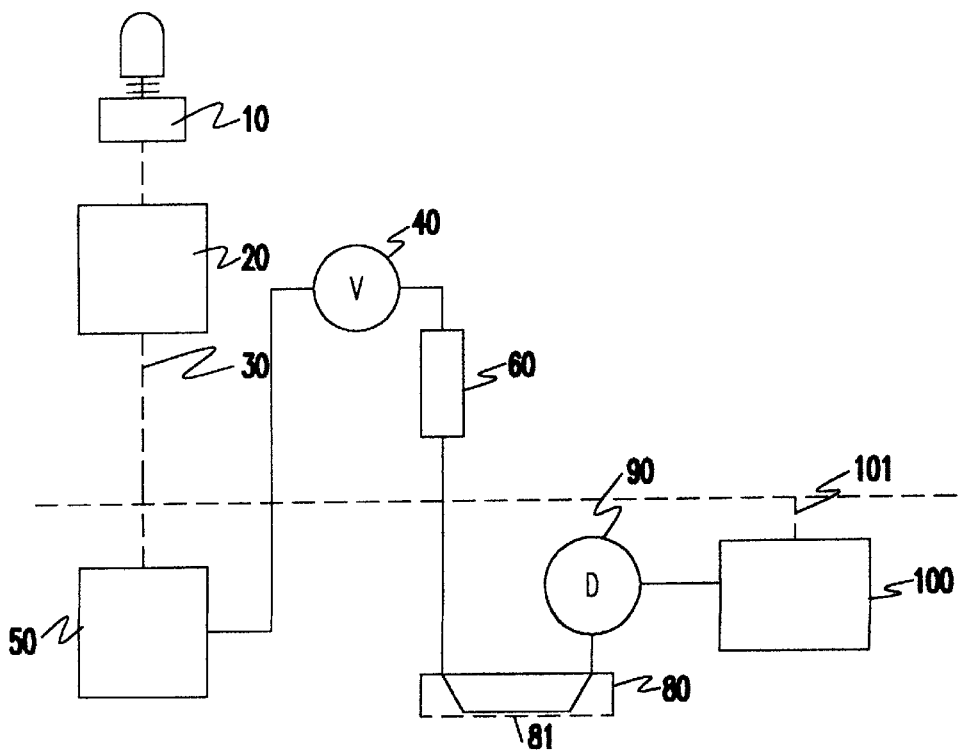

FIG. 2 shows (with corresponding referencing) a measuring system in which the pressure control valve and the throttle section were taken out of the measuring head This has the advantage that reusable parts are not replaced unnecessarily.

Figure 3:
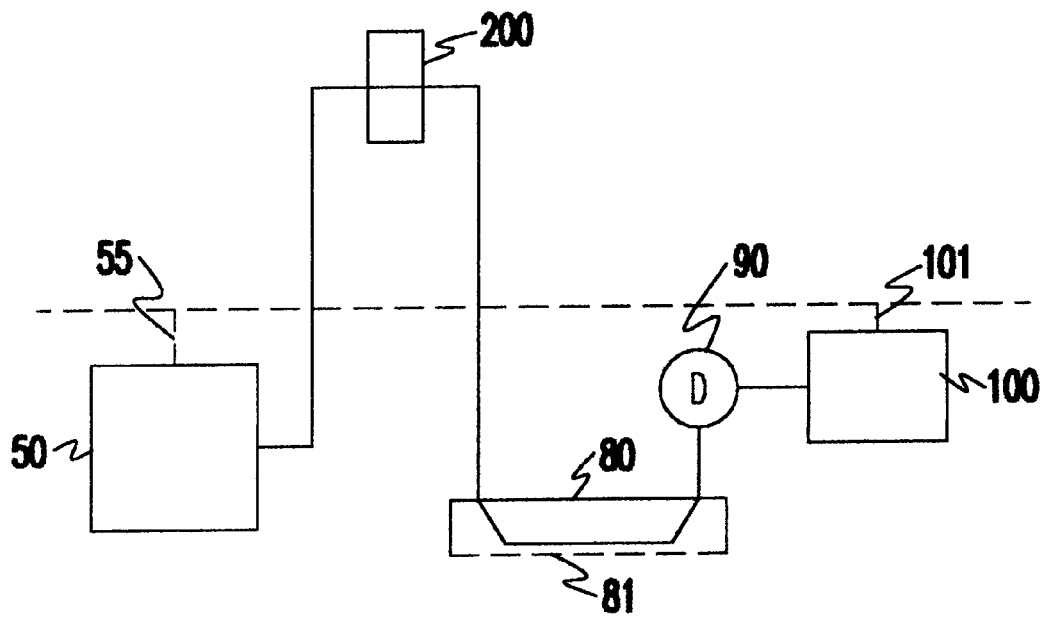

FIG. 3 shows in schematic illustration another example of construction in which the means for conveying the flow of acceptor solution including control of the flow of volume during the analysis are limited to a pump 2000. The acceptor supply reservoir can have the air removed from it via line 55 in this case.

Figure 4:
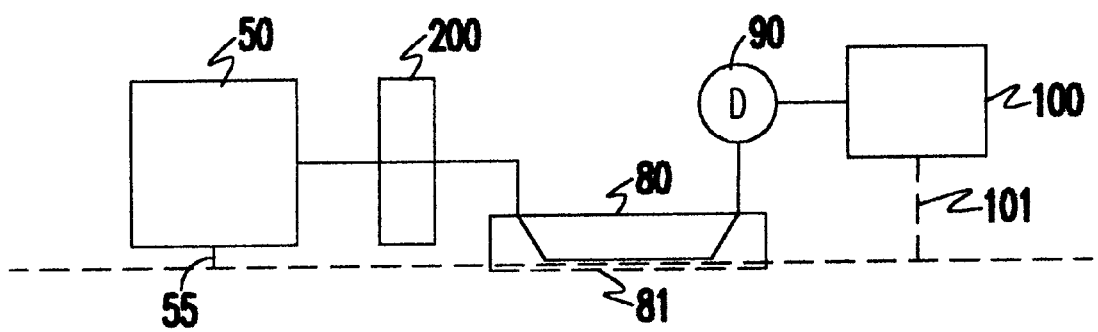

FIG. 4 shows an example of construction which corresponding to FIG. 3, is equipped with a pump for conveying the acceptor, and in which only the membrane 81 was housed in the replaceable measuring head. In general, this construction presupposes that the supply reservoir 50 is refillable and the waste receptacle 100 is able to be emptied. Furthermore, the detection system 90 in this example of construction reasonably should be stable over several measurements.

All examples of construction can be equipped with conventional components or with microfluid elements. When using microfluid elements, the measuring system can be roughly pin-shaped and of the size of a fountain-pen, whereby the measuring head is arranged in each case at the lower end of the "pin".

For Quantitative detection of substances, a calibrating device not shown here in the drawings is also required. The calibration can take place either internally at a calibrating unit existing in the measuring system or with the help of an external calibrating unit, at which the entire measuring system—with replaced measuring head under certain circumstances—is calibrated before the measurement.

Figure 5:
FIGS. 5(a–c) illustrations of measuring results in the case of alcohol measurement on human beings with a diffusion half cell placed on the skin.
Figure 5:
Figure 5:
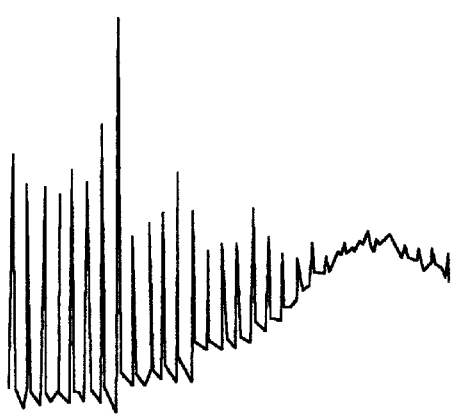

FIG. 5 shows measuring data obtained with the process according to the invention when measuring alcohol via perspiration from the skin of a test person. The time is plotted on the abscissa in each case. The measuring takes place with the membrane placed directly onto the skin. FIG. 5a) shows a comparison measurement on a person who had not consumed any alcohol; the measurement was carried out over approximately 30 minutes and illustrates the fluctuation of the reference line; on the other hand, with the same increase/the same scale on the ordinate, FIG. 5b) shows the results for an approximate 0.5 mil blood alcohol level of the person examined. It is clear that the sensitivity of the method, when compared with the noise level and the reference line fluctuations from FIG. 5a), easily allows the measuring of low blood alcohol levels as well.

Finally, FIG. 5c) shows a profile recorded over approx. 120 minutes as of alcohol delivery; this profile illustrates in exemplary manner in this case for a test person the building-up of the alcohol concentration emitted via the skin.

While the invention has been described in terms of preferred embodiments, those skilled in the art will recognize that the invention can be practiced with modification within the spirit and scope of the appended claims.

Having thus described our invention, what we claim as new and desire to secure by Letters Patent is as follows:

1. A process for detection of a substance emitted or perspired through the skin by means of a detection system responding to samples of the substance, the process using flow diffusion analysis and comprising the steps of:

flowing an acceptor medium to a diffusion half cell which is closed with a membrane, the membrane being adapted to be placed onto the skin of a person to be examined or brought into contact with a closed gas volume formed over the skin;

bringing into contact the substance to be detected and the membrane;and feeding the acceptor medium laded with the substance to be detected to the detection system for detection of the substance.

2. The process according to claim 1, further comprising maintaining the acceptor medium in the diffusion half cell for a period of time in order to bring about a defined enrichment of the substance to be detected in the acceptor medium.

3. The process according to claim 1, further comprising adding a detection reagent to the acceptor medium for determination of the substance and a detection reaction detected at the detection system.

4. The process according to claim 3, wherein a biosensor is used as the detection system.

5. The process according to claim 4, wherein the biosensor detects alcohol using alcohol oxidase (AOD) with amperometric determination of equimolecular-formed hydrogen peroxide using a platinum thick-layer electrode.

6. The process according to claim 4, further comprising calibrating the detection system before detecting the substance.

7. The process according to claim 1, wherein the substance to be detected is alcohol.

8. The process according to claim 1, further comprising providing a replaceable measuring head for housing the membrane and adapted for placing onto the skin of the person to be examined or brought into contact with the closed gas volume formed over the skin.

9. The process according to claim 1, wherein the substance to be detected permeates through the membrane and combines with the acceptor medium prior to the feeding step.

10. The process according to claim 1, further comprising detecting the substance by one of electrochemical, amperometrical and optical detection.

11. The process according to claim 1, further comprising controlling the flow of the acceptor medium.

12. The process according to claim 11, wherein the controlling of the flow of the acceptor medium includes increasing or decreasing the flow of the acceptor medium to the diffusion half cell.

13. The process according to claim 1, wherein the detecting of the substance includes measuring the substance.

* * * * *